(12) United States Patent
Keranen (10) Patent No.: US 7,936,464 B2
(45) Date of Patent: May 3, 2011

(54) DETERMINING SURFACE AND THICKNESS (75) Inventor: Heimo Keranen, Oulu (FI)

(73) Assignee: Valtion teknillinen tutkimuskeskus, Espoo (FI)

( * ) Notice: Subject to any disclaimer, the term of this patent is extended or adjusted under 35 U.S.C. 154(b) by 271 days.

(21) Appl. No.: 12/446,298

(22) PCT Filed: Oct. 17, 2007

(86) PCT No.: PCT/FI2007/050561
§ 371 (c)(1),
(2), (4) Date: Apr. 20, 2009

(87) PCT Pub. No.: WO2008/046966
PCT Pub. Date: Apr. 24, 2008

(65) Prior Publication Data
US 2010/0296107 A1 Nov. 25, 2010

(30) Foreign Application Priority Data

Oct. 18, 2006 (FI) ..................................... 20065669

(51) Int. Cl.
*G01B 11/14* (2006.01)
(52) U.S. Cl. ....................................................... 356/623
(58) Field of Classification Search .................... None
See application file for complete search history.

(56) References Cited

U.S. PATENT DOCUMENTS

| 4,458,152 A | 7/1984 | Bonora |
| 4,585,349 A | 4/1986 | Gross et al. |
| 4,936,676 A | 6/1990 | Stauffer |
| 5,162,660 A | 11/1992 | Popil |
| 5,880,846 A | 3/1999 | Hasman et al. |
| 6,064,517 A * | 5/2000 | Chuang et al. ................. 359/364 |
| 6,208,411 B1 * | 3/2001 | Vaez-Iravani .............. 356/237.2 |
| 6,268,923 B1 * | 7/2001 | Michniewicz et al. ....... 356/512 |
| 6,327,041 B1 | 12/2001 | Guern |
| 6,917,421 B1 | 7/2005 | Wihl |
| 2001/0043333 A1 | 11/2001 | Groot et al. |

(Continued)

FOREIGN PATENT DOCUMENTS

DE 3643842 6/1988

(Continued)

OTHER PUBLICATIONS

International Search Report dated Feb. 12, 2008 in PCT application.

(Continued)

*Primary Examiner* — Tu T Nguyen
(74) *Attorney, Agent, or Firm* — Young & Thompson (57) ABSTRACT

An optical radiation processing unit directs different wavelengths of the optical radiation emitted by an optical source to an object being measured from a direction that differs from the normal of a surface being measured so that the different wavelengths focus on different heights in the direction of the normal of the surface. A possible polarizer polarizes the reflected radiation in a direction perpendicular to the normal of the surface. The optical radiation processing unit directs to a detector polarized optical radiation that received from the object. The signal processing unit determines on the basis of a signal provided by the detector from the detected radiation the wavelength on which radiation is the highest, and determines the location of the surface by the determined wavelength. When measuring an object from both sides, the thickness of the object being measured is determinable using the locations of the surfaces.

25 Claims, 8 Drawing Sheets

U.S. PATENT DOCUMENTS

| | | |
|---|---|---|
| 2004/0109170 A1 | 6/2004 | Schick |
| 2006/0012804 A1 | 1/2006 | Wilke et al. |
| 2006/0028657 A1 | 2/2006 | Typpo |
| 2006/0215177 A1 | 9/2006 | Doerband |
| 2006/0232790 A1 | 10/2006 | Lee |

FOREIGN PATENT DOCUMENTS

| | | |
|---|---|---|
| DE | 19733297 | 2/1999 |
| DE | 10325942 A1 | 5/2005 |
| DE | 102004052205 A1 | 5/2006 |
| DE | 102005006724 A1 | 10/2006 |
| GB | 2043389 | 10/1980 |

OTHER PUBLICATIONS

Search Report dated Jul. 10, 2007 from corresponding FI Application No. 20065669.

European Search Report in Corresponding Application EP 07 82 3198 Dated Nov. 26, 2009.

\* cited by examiner

DETERMINING SURFACE AND THICKNESS

FIELD

The invention relates to a method for determining the surface of an object being measured and a method for determining the thickness of an object being measured. In addition, the invention relates to a measuring device for determining the surface of an object being measured and a measuring device for determining the thickness of an object being measured.

BACKGROUND

In papermaking, for instance, the thickness of paper is measured from a moving paper web. In this measurement, solutions can be used, in which the sensor of the measuring device touches the surface of the paper, or solutions in which the sensor does not touch the surface. Solutions that do not touch the surface include capacitive measurements and optical measurements. The contact of the sensor on the surface being measured may cause surface errors and, therefore, solutions in which the sensor touches the surface of the object being measured are avoided.

Optical measurements utilise chromatic aberration in determining the surface being measured. In this solution, light is focused on the surface through an optical element whose focal distance is in a known manner dependent on the wavelength of light. Light reflected from the surface is collected coaxially to a detector with the same optical element. The detector, which may be a spectrum analyser, analyses the spectrum of the reflected light. The wavelength with which the surface is best in focus is also reflected the most efficiently, and it represents the highest intensity in the spectrum. Because on the basis of the dimensioning of the measuring device, the location of the focal point of this wavelength is known, it helps define the location of the surface. If the surface is determined on both sides of the paper, it is also possible to measure the thickness of the object.

However, there are problems related to the known solution that utilises chromatic aberration. When the object being measured is of a diffuse material, light is reflected not only from the surface but also from inside the object. This causes a measurement error. For instance in measured objects into which light penetrates less, the measurement gives systematically a greater thickness than in measured objects of the same thickness into which light penetrates more. Attempts have been made to correct the measurement error computationally by altering the measuring result according to the quality of the measured objects. However, extensive corrections of measuring results reduce measuring accuracy and reliability, and an object that has not been determined in advance cannot be accurately measured.

BRIEF DESCRIPTION

It is an object of the invention to implement a method for determining the surface of an object being measured and a method for determining the thickness of an object being measured as well as measuring devices implementing the methods.

This is achieved by a measuring device for determining the surface of an object being measured using optical radiation. The measuring device comprises an optical source; an optical radiation processing unit arranged to direct different wavelengths of the optical radiation of the optical source to the object being measured from a direction differing from the normal of the surface being measured in such a manner that the different wavelengths focus on different heights in the direction of the normal of the surface being measured; a detector to which the optical radiation processing unit is arranged to direct the optical radiation that the optical radiation processing unit is arranged to receive from the object being measured at least from the direction of specular reflection that differs from the normal of the surface being measured; a signal processing unit arranged to determine from the detected optical radiation on the basis of the signal provided by the detector the wavelength on which the intensity of the optical radiation is the highest and to determine the location of the surface being measured using the determined wavelength.

The invention also relates to a measuring device for measuring the thickness of an object being measured. For measuring a first surface, the measuring device comprises an optical source; an optical radiation processing unit arranged to direct different wavelengths of the optical radiation of the optical source to the object being measured from a direction differing from the normal of the surface being measured in such a manner that the different wavelengths focus on different heights in the direction of the normal of the surface being measured; a detector to which the optical radiation processing unit is arranged to direct the optical radiation that the radiation processing unit is arranged to receive from the object being measured at least from the direction of specular reflection that differs from the normal of the surface being measured; and a signal processing unit is arranged to determine from the detected optical radiation on the basis of the signal provided by the detector the wavelength on which the intensity of the optical radiation is the highest and to determine the location of the surface being measured using the determined wavelength; and for measuring a second side of the object being measured, the measuring device comprises: a second-side optical source; a second-side optical radiation processing unit arranged to direct different wavelengths of the optical radiation of the optical source to the object being measured from a direction differing from the normal of the surface being measured in such a manner that the different wavelengths focus on different heights in the direction of the normal of the surface being measured; a second-side detector to which the optical radiation processing unit is arranged to direct the optical radiation that the optical radiation processing unit is arranged to receive from the object being measured at least from the direction of specular reflection that differs from the normal of the surface being measured; and a signal processing unit is arranged to determine from the detected optical radiation on the basis of the signal provided by the second-side detector the wavelength on which the intensity of the optical radiation is the highest and to determine the location of a second surface being measured using the determined wavelength; and the signal-processing is arranged to measure the thickness of the object being measured by means of the determined locations of the surfaces.

The invention further relates to a method for determining the surface of an object being measured by means of optical radiation. The method comprises directing different wavelengths of optical radiation to the object being measured from a direction differing from the normal of the surface being measured in such a manner that the different wavelengths focus on different heights in the direction of the normal of the surface being measured; receiving optical radiation at least from the direction of specular reflection that differs from the normal of the surface being measured; determining from the received optical radiation the wavelength on which the intensity of the received optical radiation is the highest; and determining the location of the surface of the object being measured by means of the determined wavelength.

The invention also relates to a method for measuring the thickness of an object being measured by using optical radiation. The method comprises directing different wavelengths of optical radiation to the object being measured from a direction differing from the normal of a first surface being measured in such a manner that the different wavelengths focus on different heights in the direction of the normal of the first surface being measured; receiving optical radiation at least from the direction of specular reflection that differs from the normal of the first surface being measured; determining from the received optical radiation the wavelength on which the intensity of the received optical radiation is the highest; and determining the location of the first surface being measured by means of the determined wavelength; directing different wavelengths of optical radiation to the object being measured from a direction differing from the normal of a second surface being measured in such a manner that the different wavelengths focus on different heights in the direction of the normal of the second surface being measured; receiving optical radiation at least from the direction of specular reflection that differs from the normal of the second surface being measured; determining from the received optical radiation the wavelength on which the intensity of the optical radiation is the highest; and determining the location of the second surface being measured by means of the determined wavelength; and determining the thickness of the object being measured by using the determined locations of the surfaces.

Preferred embodiments of the invention are disclosed in the dependent claims.

The methods and measuring devices of the invention provide several advantages. It is possible to reduce the diffuse reflection coming from inside the object being measured, which disturbs the measurement. The surface and thickness of an object being measured can thus be determined accurately regardless of the diffuse reflection.

LIST OF FIGURES

The invention will now be described in greater detail by means of preferred embodiments and with reference to the attached drawings, in which.

DESCRIPTION OF EMBODIMENTS

The present solution can be applied to measuring diffuse materials in particular, even though the measurement also works with undiffused materials. Diffuse materials include paper, textiles, metal coated with a diffuse material, skin, various powders whose surface (or thickness) needs to be determined.

Figure 1:
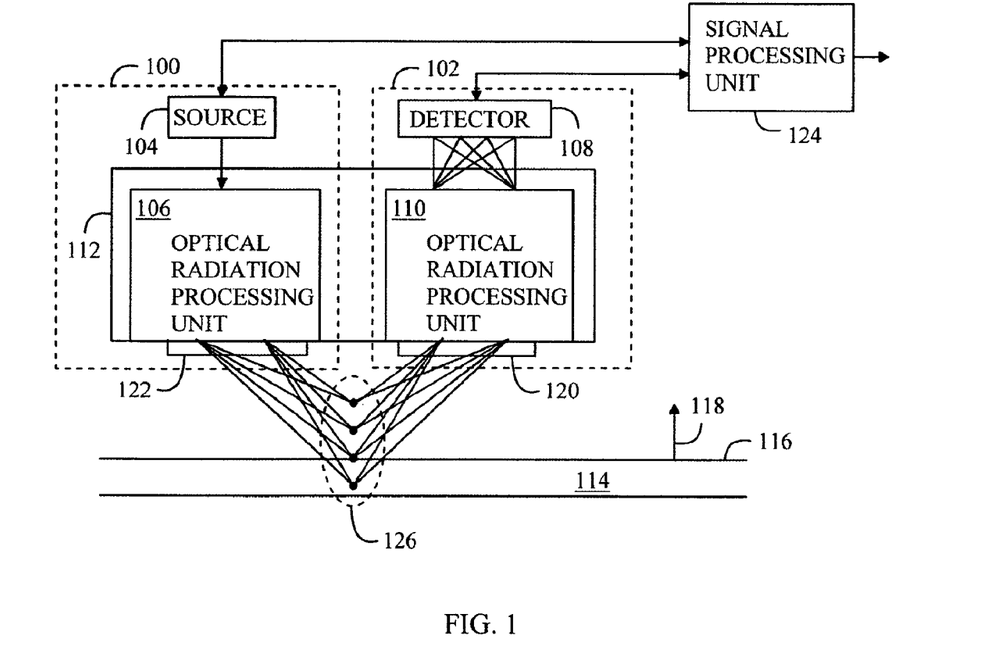
FIG. 1 shows a measuring device whose detector receives dispersed optical radiation.

Let us now examine the present solution by means of FIG. 1 in which a measuring device comprises a transmitter part 100 and receiver part 102 that are separate from each other. The transmitter part 100 comprises an optical source 104 and a first optical radiation processing part 106. In this application, optical radiation refers to electromagnetic radiation whose wavelength band is between ultraviolet radiation (wavelength approximately 50 nm) and infrared radiation (wavelength approximately 1 mm). The receiver part 102 comprises a detector 108 and a second optical radiation processing part 110. The optical radiation processing parts 106 and 110 form an optical radiation processing unit 112 in which the optical radiation processing part 106 directs different wavelengths of optical radiation coming from the optical source to an object 114 being measured from a direction differing from the normal 118 of a surface 116 being measured in such a manner that the different wavelengths are directed to (focused on) different heights in the direction of the normal 118 of the surface 116 being measured. Even though the surface was rough, as it often is, normal refers to a mean normal direction obtained for instance by averaging a large number of representative normals. Some of the wavelengths may focus above the object 114 being measured and some inside it. The optical radiation can be dispersed into separate wavelengths by means of a prism or grid in the optical radiation processing part 106. Directing can in turn be done using one or more lenses or mirrors to focus different wavelengths on different focal points 126.

The measuring device comprises at least one polarizer 120, 122. Because it is possible to work with just one polarizer, the polarizer 122 of the transmitter part 100 is not necessarily needed and polarizer 120 can be used to polarize the optical radiation reflected from the object 114 being measured perpendicular to the normal 118 of the surface 116 being measured. The vibration of the electric field of optical radiation then has a perpendicular component in relation to the normal 118 of the surface 116. When several polarizers are used, the polarization directions of all polarizers are the same. One or more polarizers attenuate the optical radiation coming from inside the object 114 being measured, because inside the object 114 being measured polarization weakens or disappears. Optical radiation reflected from a surface is polarized or maintains its polarization.

In this application, reflection refers to specular reflection and diffuse reflection in which reflection may take place from a smooth or rough surface. In addition, reflection also refers herein to scattering, refracting and reflecting radiation from inside the object being measured. In an embodiment, optical radiation can be directed to a surface and received at a Brewster angle, whereby the optical radiation is most effectively polarized as it is reflected from the surface.

The optical radiation processing part 110 of the optical radiation processing unit 112 can focus received polarized optical radiation to a detector 118 by means of one or more lenses or mirrors. The optical radiation processing part 110 and detector 108 are directed and the numerical aperture of the optical radiation processing part 110 and detector 108 is dimensioned in such a manner that polarized optical radiation can be received at least from the direction of specular reflection from the object 114 being measured. In the case of FIG. 1, the focal points of the different wavelengths of dispersed optical radiation are in parallel on the detector 108. For this reason, the different wavelengths in the solution of FIG. 1 can be detected with a line detector, for example. Thus, each wavelength is directed to one detector element of the line detector.

An electric signal generated by the detector 108 from optical radiation can be fed to a signal processing unit 124 that can define from the received optical radiation the wavelength on which the intensity of the received optical radiation is the highest. Similarly, the signal processing unit 124 can determine the location of the surface 116 of the object 114 being measured using the determined wavelength. The definition of the surface 116 being measured is based on knowing in advance at which distance each wavelength is focused, and assuming that the wavelength that is reflected from the focal point is the strongest.

Figure 2:
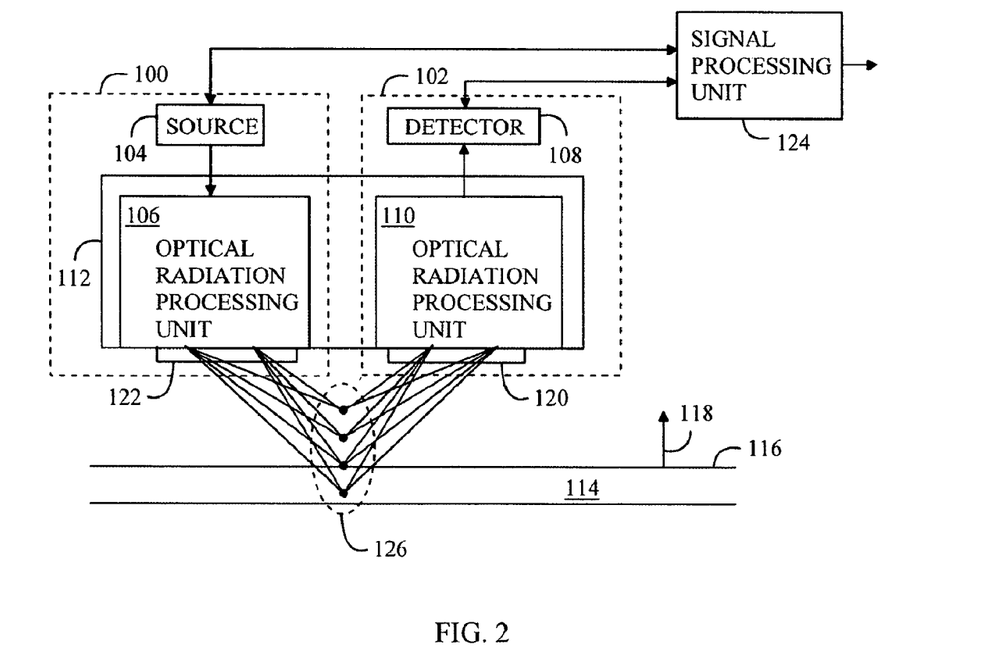
FIG. 2 shows a measuring device whose detector receives undispersed optical radiation.

FIG. 2 shows a solution, in which a second optical radiation processing part 110 also comprises a dispersive component, such as a prism or grid, with which the wavelengths of optical radiation propagating along different routes can be assembled. Different wavelengths then arrive at the same focal point at the detector 108, and the detector 108 can be just one element.

Figure 3:
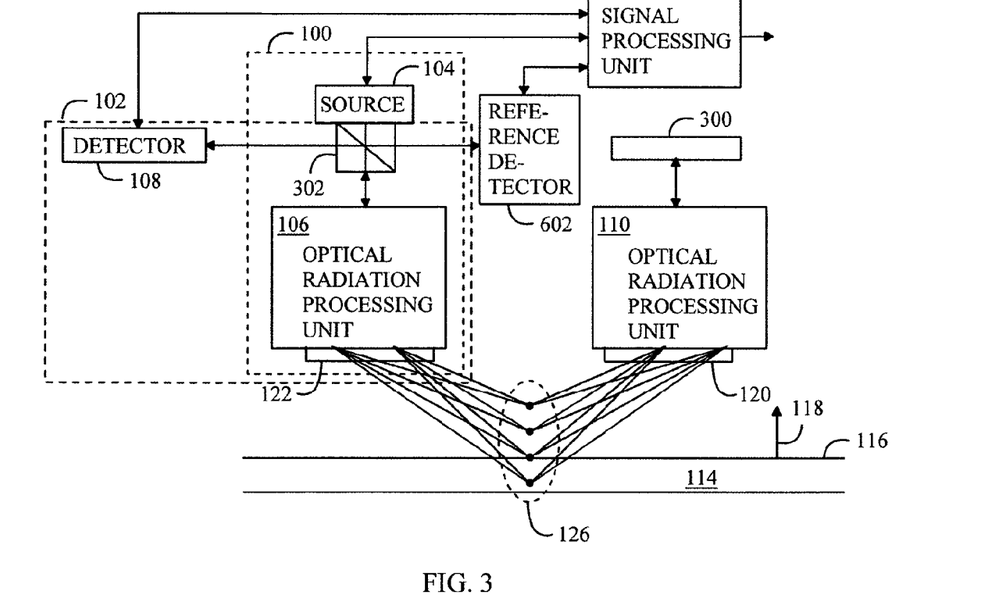
FIG. 3 shows a measuring device with a reflector.

FIG. 3 shows a solution in which a measuring device comprises an optical radiation processing unit 112 with a common transmitter part 100 and receiver part 102. In this solution, the propagation of optical radiation from the optical source 104 to the object 114 being measured and on to the optical radiation processing part 110 takes place in the same manner as in the case of FIG. 2. The optical radiation reflected once from the object 114 being measured does not, however, propagate directly to the detector 108, but the measuring device comprises a reflector 300 that reflects the optical radiation reflected from the object 114 being measured back to the object 114 being measured to reflect on from the object 114 being measured via a second optical radiation processing part 110 towards the first optical radiation processing part 106 and on towards the optical source 104. In the solution of FIG. 3, the measuring device comprises a beam splitter 302 that directs at least part of the optical radiation directed towards the optical source 104 to the detector 108. The beam splitter 302 can be a polarizing beam splitter, in which case the beam splitter 302 also polarizes the optical radiation directed to the object 114 being measured and no separate polarizers 120, 122 are required. The beam splitter 302 can then also direct all polarized optical radiation from the reception direction to the detector 108.

Alternatively, the beam splitter 302 may be based on solely distributing the optical power in a desired ratio, whereby separate optical beams usually obtain the same power. In such a case, either of the separate polarizers 120, 122 is needed.

Figure 4:
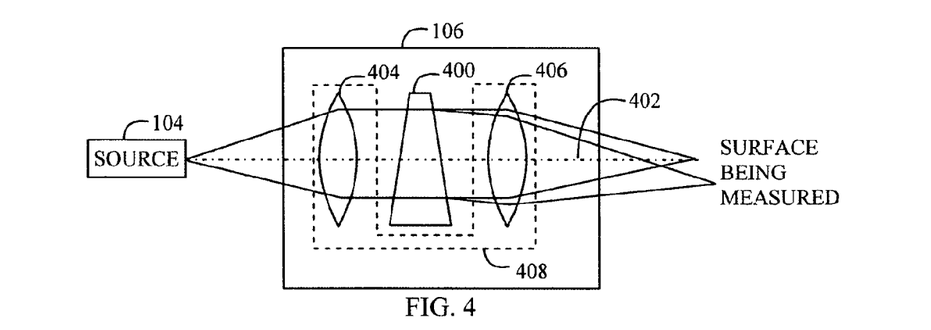
FIG. 4 shows an optical radiation processing part.

FIG. 4 shows an optical radiation processing part 106. To direct the different wavelengths of optical radiation coming from the optical source 104 in different ways to the object 114 being measured, the first optical radiation processing part 106 may comprise a chromatically dispersive component 400 that is arranged to disperse non-axially the optical radiation directed to the object 114 being measured. Optical radiation is thus dispersed with the dispersive component 400 in a direction differing from the optical axis 402 of the first optical radiation processing part 106, whereby the dispersion, that is, the distribution of the wavelengths, is at least partly directed in the direction of the normal 118 of the surface 116 being measured. The direction of the focal points does not need to be parallel to the normal 118 of the surface 116, but the directions have a common vector component (i.e. the focal points are not horizontal nor on an optical axis). In the solution of FIG. 4, the dispersive component 400 is located between two focusing lenses 404, 406. The lenses 404, 406 form a focusing component 408. Radiation coming from the optical source 104 between the lenses can be collimated. The dispersive component 400 together with the focusing component 408 may focus the different wavelengths of the optical radiation of the optical source 104 on different heights in the direction of the normal 118 of the surface 116 being measured. The dispersing component 400 may be a prism or grid, and instead of lenses or in addition to them, focusing mirrors can be used. Both lenses 404, 406 can be replaced with a lens combination, mirror, mirror combination, or a combination of all these.

Figure 5:
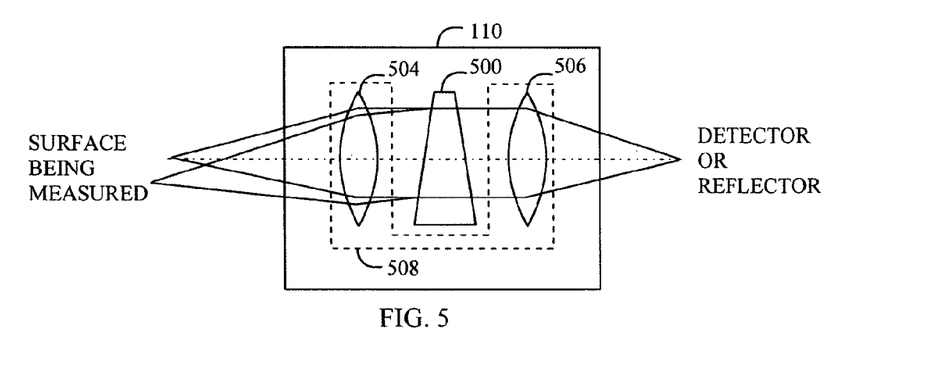
FIG. 5 shows an optical radiation processing part.

FIG. 5 shows an optical radiation processing part 110. Optical radiation reflected from the object 114 being measured can be focused on the detector 108 with the focusing component 508 that comprises lenses 504, 506. The focal point of the second optical radiation processing part 110 can be on the surface 116 being measured or near it. Without the dispersive component 500, the depth of field should be sufficiently good around the focal point.

The optical radiation processing part 110 may also comprise a dispersive component 500 that removes dispersion and enables the combination of wavelengths propagated along different optical paths to the same focus. The focal points in front of the second optical radiation processing part 110 can be at the same points as those to which the first optical radiation processing part 106 focuses different wavelengths (see FIG. 1, for example). The reflection from the surface 116 being measured is then effective. When using a dispersive component 500, the dispersed wavelengths focus behind the second optical radiation processing part 110 at the same focal point, for instance at the detector 108, and the detection can be done with one detector element. When using a reflector 300, it can be at the focus of the second optical radiation processing part 110, or optical radiation can be reflected directly back from the back part (lens 506) of the second optical radiation processing part 110 towards the object 114 being measured. The first 106 and second 110 optical radiation processing parts may be alike, but the strengths and dispersive component 400 of the lenses 404, 406 may also differ from each other.

The second optical radiation processing part 110 may comprise a second dispersive component 500 that removes dispersion from the optical radiation reflected from the object 114 being measured. The second optical radiation processing part 110 can focus the optical radiation in an undispersed form to the detector 108.

In the embodiment (see FIG. 2) in which only the optical radiation processing part 106 has a dispersive component 400, and a reflector 300 is not used, the detector 108 may be a line detector and a different wavelength of undispersed optical radiation is directed to each of its elements. In this case, as in general, a single wavelength refers to a narrow wavelength band that is only part of the measuring band. A narrow band can be for instance a band that is less than one fifth of the entire measuring band. Often a narrow band is only a nanometer or dozens of nanometers wide. A narrow band may be defined on the basis of the desired measuring accuracy, or it may be determined by the measuring accuracy of the measuring devices and components.

In the embodiment (see FIG. 3) that uses a reflector 300, the reflector may reflect optical radiation back to the object 114 being measured through the optical radiation processing part 110. The second optical radiation processing part 110 may then focus different wavelengths of optical radiation on different heights in the direction of the normal 118 of the surface 116 being measured. When both optical radiation processing parts 106 and 110 comprise dispersive components 400 and 500, undispersed optical radiation is directed to the detector 108.

Figure 6:
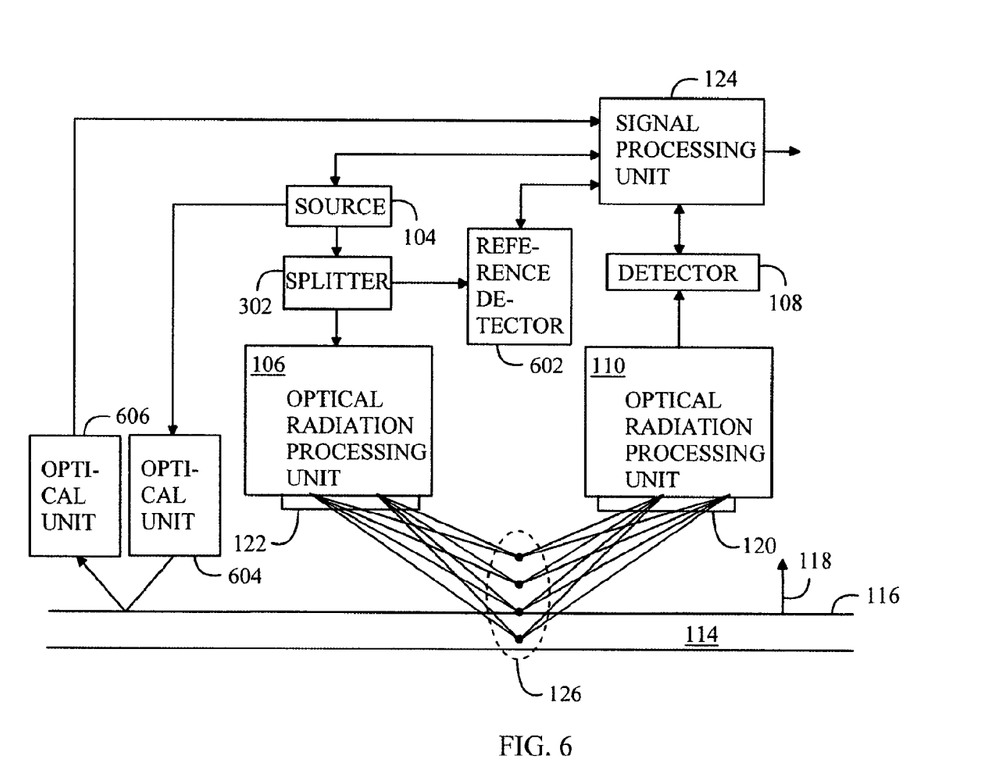
FIG. 6 shows the normalization of a measurement.

FIG. 6 shows the measurement of a reference. Since the intensities of the different wavelengths of the source 104 are not evenly distributed and different wavelengths may have a different intensity, the intensity distribution of the source 104 may be measured as a function of the wavelength. In such a case, between the source 600 and optical radiation processing part 106 there may be a reference beam splitter 600 that directs part of the optical radiation emitted by the source 104 to a reference detector 602 that transforms the received optical radiation into an electric signal. The beam splitter 600 may also be part of the optical radiation processing part 106. The signal processing unit 124 receives the electric signal. Because the signal processing unit 124 also receives a measuring signal of the object 114 generated by the detector 108, the signal processing unit 124 may normalize the measurement made by the detector 108 with the measurement made by the reference detector 602. Normalization may mean, for instance, the division of the intensities obtained with the detector 108 by the intensities measured by the reference detector 602. The reference beam splitter 600 can be the same as the directional beam splitter 302 in FIG. 3. The directional beam splitter 302 may also act as the reference beam splitter 600.

FIG. 6 also shows an embodiment with which it is possible to compensate for the colour of the object 114 being measured, or generally the reflection response of the object 114 being measured. An optical unit 604 may direct optical radiation produced by the source 104 in an undispersed form to the object 114 being measured, and optical radiation reflected therefrom can be received with another optical unit 606 that comprises a detector. The optical unit 606 may form a spectrum of the reflected radiation which the signal processing unit 124 may measure. The optical unit 606 may feed an electric signal of the measurement to the signal processing unit 124 and the unit 124 may normalize the measuring result obtained with the detector 108 with at least one of the following: the measuring result of the reference detector 124, the measuring result of the optical unit 606.

Figure 7:
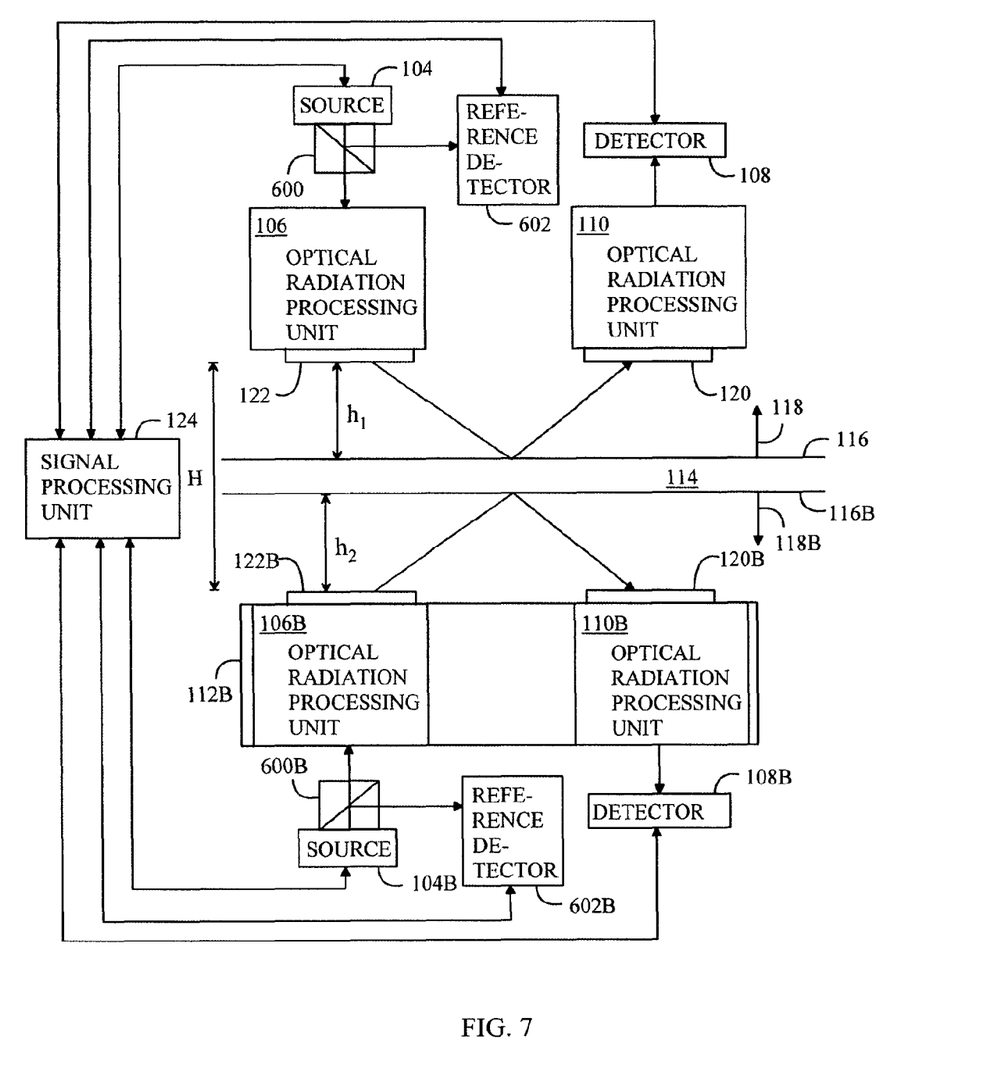
FIG. 7 shows the measurement of the thickness of an object.

FIG. 7 shows an embodiment in which both surfaces 116, 116B of the object being measured are measured in the manner described above. The optical source then directs optical radiation through the optical radiation processing part 106 to the object 114 being measured in such a manner that the different wavelengths focus at different distances in the direction of the normal 118 of the surface 116 being measured. Optical radiation is reflected from the object 114 being measured to the optical radiation processing part 110 through the polarizer 120, for instance. It is also possible to use both polarizers 120, 122. The optical radiation processing part 110 directs the reflected optical radiation to the detector 108. The detector 108 feeds the measuring signal to the signal processing unit 124 for surface determination. The intensity distribution of the optical source 104 in relation to the wavelengths can be measured using the beam splitter 600, reference detector 602, and signal processing unit 124. Instead of the one or more polarizers 120, 122 or in addition to them, the beam splitter 600 can be a polarizer.

Correspondingly, the second surface 116B of the object 114 being measured can be determined by focusing different wavelengths generated by the optical source 104B and optical radiation processing unit 106B at different distances in the direction of the normal 118B of the surface 116B being measured. Optical radiation is reflected from the object 114 being measured to the optical radiation processing part 110B through the polarizer 120B, for instance. It is also possible to use both polarizers 120B, 122B. The optical radiation processing part 110 directs the reflected optical radiation to the detector 108B. The detector 108 feeds the measuring signal to the signal processing unit 124 for surface determination. The intensity distribution of the optical source 104B in relation to the wavelengths can be measured using the beam splitter 600B, reference detector 602B, and signal processing unit 124. Instead of the one or more polarizers 120B, 122B or in addition to them, the beam splitter 600B can be a polarizer. Each block 104B to 110B, 120B, 122B, 600B, 602B below the object being measured is the same as blocks depicted by reference numbers 104 to 110, 120, 122, 600, 602 in FIGS. 1 to 6. Naturally, blocks 104 to 110, 120, 122, 600, 602 in FIG. 7 are also similar to those in the previous figures, but the top measuring part in FIG. 7 need not be the same as the bottom measuring part. For instance, it is possible to use both polarizers above the object being measured, but below it only one polarizer 120B may be used. FIG. 7 shows that both above and below the object being measured there is a measuring principle corresponding to FIG. 2. Naturally, it is also possible to use either above or below or in both places a measuring principle corresponding to FIG. 3, where a reflector 300 is utilized.

When the location $h_1$ of the top surface has been determined in relation to the top measuring part, and the location $h_2$ of the bottom surface has been determined in relation to the bottom measuring part, and when the predetermined distance H between the top and bottom measuring parts is known, it is possible to determine the thickness T of the object 114 being measured for instance by subtracting from the distance H the values of the surface locations $h_1$ and $h_2$, that is $T=H-(h_1+h_2)$.

Figure 8:
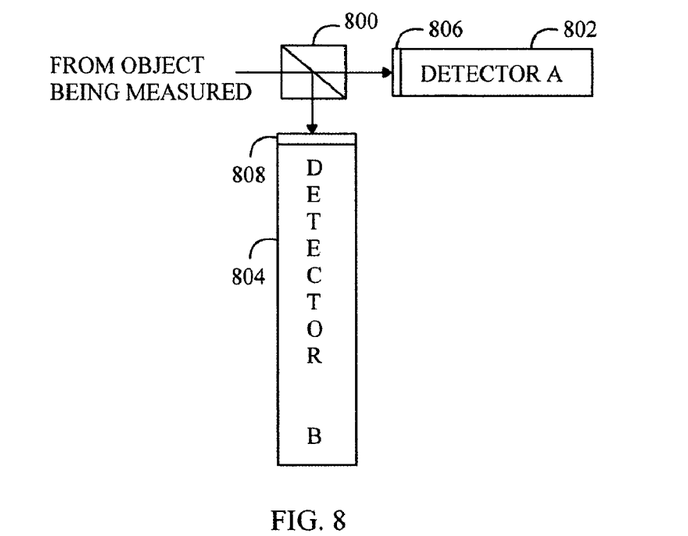
FIG. 8 shows spectrum detection by means of a beam splitter, two different filters, and two detectors.
Figure 9:
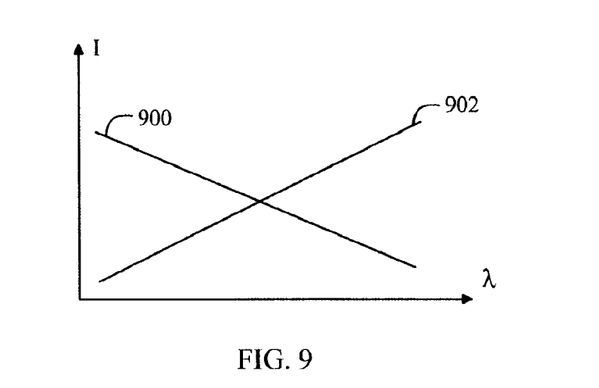
FIG. 9 shows filter permeability.

FIG. 8 shows detecting by means of two detector parts. The detector 108 may comprise a detector beam splitter 800 that distributes at a known ratio the optical radiation it receives from the object 114 being measured to two detector parts 802 and 804. Filters 806, 808 are located in front of the detector parts 800, 802 to filter the radiation arriving at the detectors as shown in FIG. 9. The solution can also be applied to the reference detector 602.

FIG. 9 shows pass curves of filters in relation to the wavelength. The vertical axis shows the intensity I and the horizontal axis shows the wavelength λ. Curve 900 shows the response of filter 806 in relation to the wavelength and curve 902 the response of filter 808 in relation to the wavelength. Filter 806 may pass less on a short wavelength than on a long wavelength and conversely, filter 808 may pass less on a long wavelength than on a short one, and the curves may be linear. The response of filter 806 is in general different from that of filter 808 on the band used in measurement. When the optical power (or intensity) detected by both detectors on each wavelength is summed and divided by the difference in detected optical powers, the wavelength that is reflected from the surface 116 of the object 114 being measured is at the greatest relative intensity among the thus formed relative intensities. Mathematically the following formula, for example, can be created: $P_{rel}=P_{detA}-P_{detB}:P_{detA}+P_{detB}$, wherein $P_{rel}$ refers to relative intensity (or power), $P_{detA}$ refers to the power detected by detector 800, and $P_{detB}$ refers to the power detected by detector 802. In a simpler manner, the relative intensities can be formed by dividing the powers detected by each detector, that is, $P_{rel}=P_{detA}:P_{detB}$.

Figure 10:
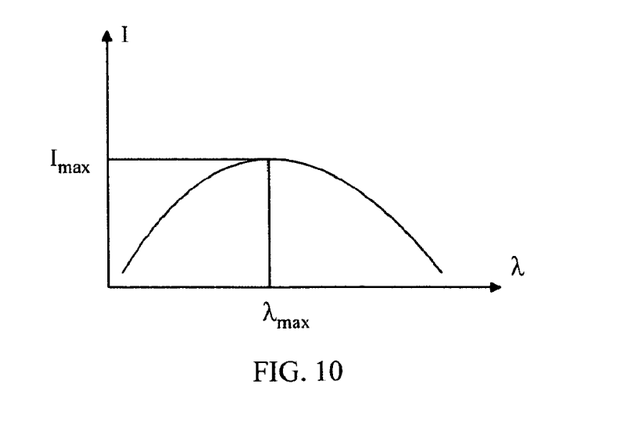
FIG. 10 shows a detected spectrum.

FIG. 10 shows a measured spectrum showing intensity I as a function of wavelength λ. When the signal processing unit 124 finds wavelength $\lambda_{max}$ with the highest intensity, it is possible to determine the distance of the surface 116 (or 116B) being measured from a predefined point by using for instance a linear calculation $h_1=k\cdot\lambda_{max}$, where k is a predefined constant. Dependency on the wavelength $\lambda_{max}$ of the highest intensity can also be nonlinear, but for determining the location of the surface, it is sufficient that the dependency is known.

Figure 11:
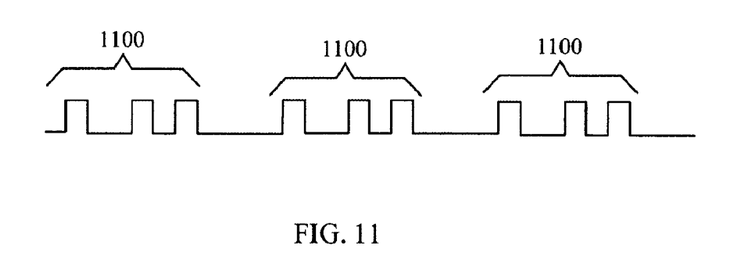
FIG. 11 is an example of the modulation of optical radiation.

FIG. 11 shows an example of modulating optical radiation. Optical radiation emitted by the source 104 can be modulated. Modulation can be performed with a mechanical, electro-optical, magneto-optical, or acousto-optical chopper/modulator, or the modulation can be done electronically (in a diode, for instance). The modulation may be time-divided, whereby the optical source 104 emits optical pulses regularly, pseudo-randomly or randomly. Regular pulsing may mean repetitive, regular transmission of a predefined pulse pattern 1100, or at its simplest the transmission of pulses at a desired frequency. The interval between the pulses of a predefined pulse pattern may be regular or irregular. Between the pulses the optical source 104 does not emit optical radiation at all, or the optical power between the optical pulses is lower than during the pulse. The signal processing unit 124 may control modulation and correspondingly and in a synchronized manner demodulate the signal arriving from the detector 108. When using modulation, the impact of interference to the measurement is reduced. Using modulation may be beneficial when measuring an object 114 on both its sides. It is then possible to direct optical radiation to different sides of the object 114 being measured at different times or use a different modulation. This way, the optical radiation from the opposite side does not disturb the measurement.

Figure 12:
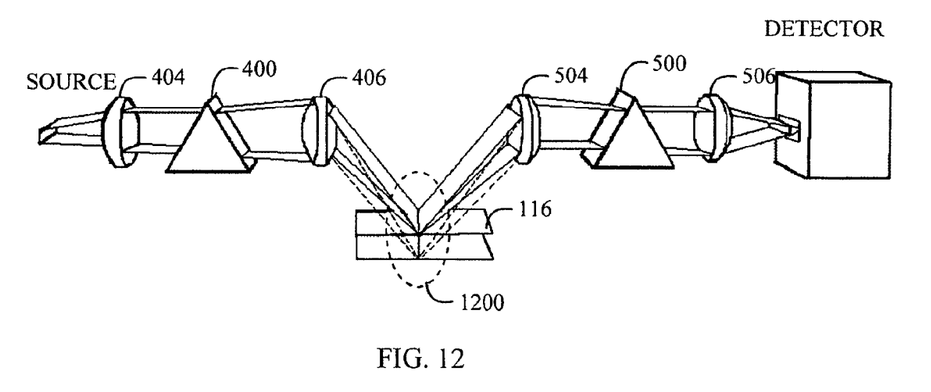
FIG. 12 shows measurement using a focal point line system.

FIG. 12 shows an embodiment in which the optical radiation processing part 106 together with the focusing optical components 404, 406 and dispersive component 400 can form, instead of focal points, a focal point line system 1200 in which each wavelength is focused on its own line. The source is then a dotted or linear source. It is possible to use as the focusing components 404, 406 lenses with spherical surfaces or in some cases even cylinder lenses. Correspondingly, the optical radiation processing part 110 may comprise optical components 504, 506, and a dispersive component 500 that divide the focal point line system 1200 in the direction of the normal of the surface 116 being measured.

Each wavelength used in the measurement can be directed to the object 114 being measured simultaneously or at different times. The wavelengths can be directed to the object 114 being measured in small groups (or bands) or one wavelength at a time. Each wavelength or wavelength band can be formed using suitable, replaceable or adjustable filters, or the band of the optical source can be swept over the measuring band. For instance, a led band may be 20 nm and it can be swept over the measuring band that may be 500 to 650 nm. The monochromatic wavelength of a laser can also be swept over dozens or hundreds of nanometers, for instance.

The optical source 104 may comprise an incandescent lamp, gas-discharge lamp, halogen lamp, led, or a laser with adjustable wavelength, etc. The optical source 104 may also comprise an optical fibre, in which case the actual unit generating the optical radiation may be far from the optical radiation processing unit 106 and the object 114 being measured.

The detector 108 may in turn comprise any device forming a spectrum, for instance a spectrograph. In the solution of FIG. 8, the detector may also comprise a PIN diode, APD (avalanche photodiode), LDR (light dependent resistor), photomultiplier tube, CCD (charge coupled device) cell, CMOS (complementary metal oxide semiconductor) cell, pyrodetector, or the like. The detector 108 may also comprise a fibre with which optical radiation can be transferred to the actual detecting unit.

Figure 13:
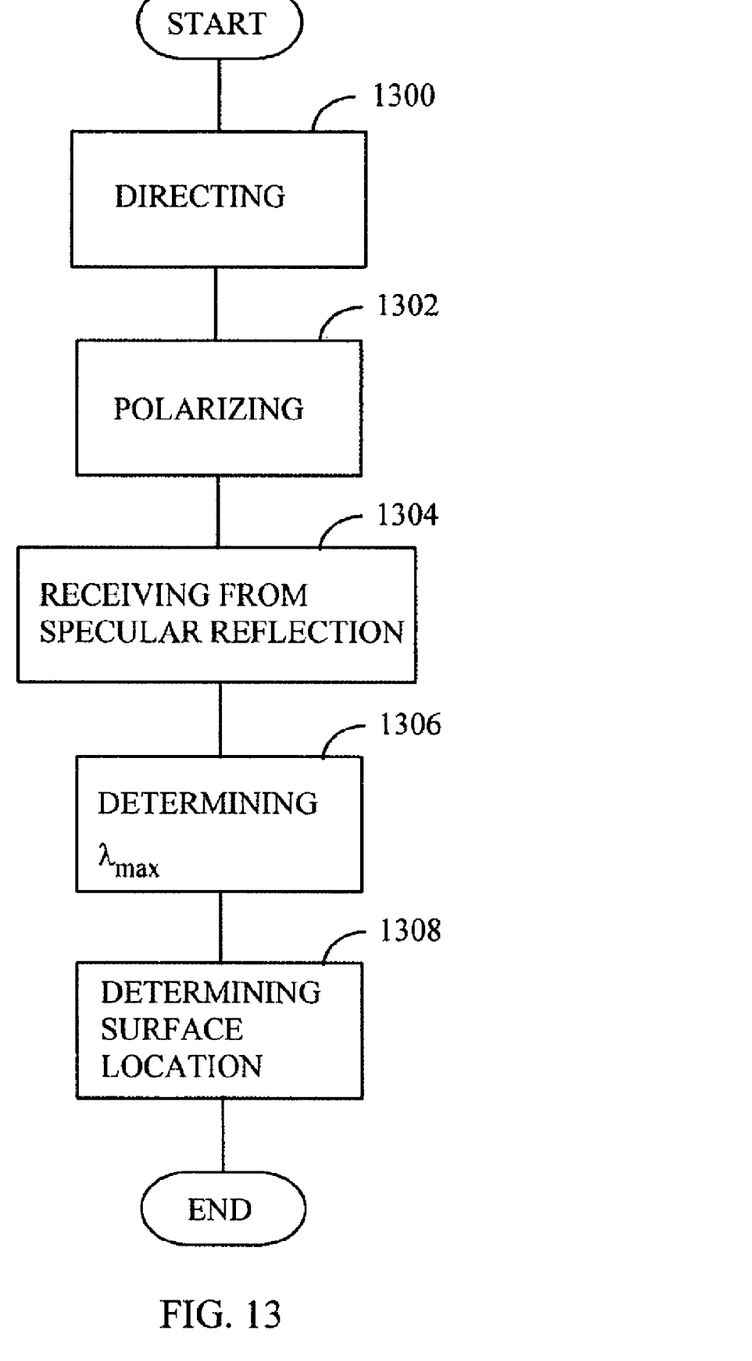
FIG. 13 is a flow chart of a surface determination method.

FIG. 13 shows a flow chart of a method of determining the surface of an object being measured. In step 1300, different wavelengths of optical radiation are directed to an object 114 being measured from a direction differing from the normal 118 of a surface 116 being measured in such a manner that the different wavelengths focus on different heights in the direction of the normal 118 of the surface 116 being measured. In step 1302, optical radiation reflected from the object 114 being measured can be polarized to a direction perpendicular to the normal 118 of the surface 116 being measured. In step 1304, polarized optical radiation is received at least from the direction of specular reflection that differs from the normal 118 of the surface 116 being measured. In step 1306, the wavelength on which the intensity of the received optical radiation is the highest is determined from the received optical radiation. In step 1308, the location of the surface 116 of the object 114 being measured is determined by means of the determined wavelength.

Figure 14:
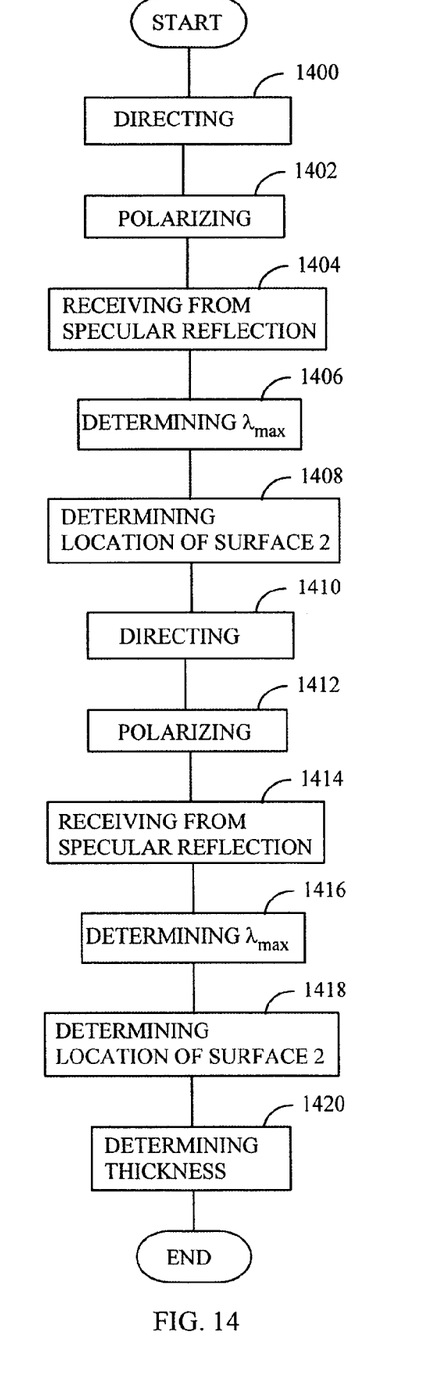
FIG. 14 is a flow chart of a thickness measurement method.

FIG. 14 shows a flow chart of a method of determining the thickness of an object being measured. In step 1400, different wavelengths of optical radiation are directed to an object 114 being measured from a direction differing from the normal 118 of a first surface 116 being measured in such a manner that the different wavelengths focus on different heights in the direction of the normal 118 of the surface 116 being measured. In step 1402, optical radiation reflected from the object 114 being measured can be polarized to a direction perpendicular to the normal 118 of the first surface 116 being measured. In step 1304, polarized optical radiation is received at least from the direction of specular reflection that differs from the normal 118 of the first surface 116 being measured. In step 1406, the wavelength on which the intensity of the received optical radiation is the highest is determined from the received optical radiation. In step 1408, the location of the surface 116 being measured is determined by means of the determined wavelength. In step 1410, the different wavelengths of optical radiation are directed to the object 114 being measured from a direction differing from the normal 118B of a second surface 116B being measured in such a manner that the different wavelengths are directed to different heights in the direction of the normal 118B of the second surface 116B being measured. In step 1412, optical radiation reflected from the object 114 being measured can be polarized to a direction perpendicular to the normal 118B of the second surface 116B being measured. In step 1414, polarized optical radiation is received at least from the direction of specular reflection that differs from the normal 118B of the second surface 116B being measured. In step 1416, the wavelength on which the intensity of the received optical radiation is the highest is determined from the received optical radiation. In step 1418, the location of the second surface 116B being measured is determined by means of the determined wavelength. In step 1420, the thickness of the object 114 being measured is determined by means of the determined locations of the surfaces 116, 116B.

Even though the invention is above described with reference to the examples according to the attached drawings, it is apparent that the invention is not limited to them, but may be modified in many ways within the scope of the attached claims.

The invention claimed is:

1. A measuring device for determining the surface of an object being measured using optical radiation, the measuring device comprising
   an optical source;
   an optical radiation processing unit arranged to direct different wavelengths of the optical radiation of the optical source to the object being measured from a direction differing from the normal of the surface being measured in such a manner that the different wavelengths focus on different heights in the direction of the normal of the surface being measured;
   a detector to which the optical radiation processing unit is arranged to direct the optical radiation that the optical radiation processing unit is arranged to receive from the object being measured at least from the direction of specular reflection that differs from the direction of the normal of the surface being measured;
   a signal processing unit arranged to determine from the detected optical radiation on the basis of the signal provided by the detector the wavelength on which the intensity of the optical radiation is the highest and to determine the location of the surface being measured using the determined wavelength.

2. A measuring device as claimed in claim 1, wherein the measuring device comprises at least one polarizer, and at least one polarizer is arranged to polarize optical radiation reflected from the object being measured in a direction perpendicular to the normal of the surface being measured.

3. A measuring device as claimed in claim 2, wherein the beam splitter is arranged to act as a polarizer.

4. A measuring device as claimed in claim 1, wherein the optical radiation processing unit comprises a first optical radiation processing part for directing optical radiation to the object being measured and a second optical radiation processing part for directing optical radiation reflected from the object being measured to the detector.

5. A measuring device as claimed in claim 4, wherein the first optical radiation processing part comprises a dispersive component that is arranged to disperse optical radiation directed to the object being measured chromatically in a non-axial direction;
   the first optical radiation processing part comprises a first focusing component that is arranged to focus the different wavelengths of the non-axially dispersed optical radiation on different heights in the direction of the normal of the surface of the object being measured; and
   the second optical radiation processing part comprises a second dispersive component that is arranged to remove dispersion from the optical radiation reflected from the object being measured; and
   the second optical radiation processing part comprises a second focusing component that is arranged to focus optical radiation in an undispersed form to the detector.

6. A measuring device as claimed in claim 4, wherein the first optical radiation processing part comprises a dispersive component that is arranged to disperse optical radiation directed to the object being measured chromatically in a non-axial direction;
   the first optical radiation processing part comprises a first focusing component that is arranged to focus the different wavelengths of the non-axially dispersed optical radiation on different heights in the direction of the normal of the surface of the object being measured; and
   the second optical radiation processing part comprises a second focusing component that is arranged to focus optical radiation in a dispersed form to the detector.

7. A measuring device as claimed in claim 1, wherein the optical radiation processing unit comprises a first optical radiation processing part, a second optical radiation processing part, a reflector and a directional beam splitter;
   the first optical radiation processing part being arranged to direct optical radiation to the object being measured;
   the second optical radiation processing part being arranged to direct optical radiation reflected from the object being measured to the reflector that is arranged to reflect optical radiation reflected from the object being measured back to the object being measured through the second optical radiation processing part that is arranged to direct different wavelengths of optical radiation to the object being measured from a direction differing from the normal of the surface being measured in such a manner that the different wavelengths focus on different heights in the direction of the normal of the surface being measured, while one wavelength focuses on the surface being measured;
   the first optical radiation processing part being arranged to direct optical radiation reflected from the object being measured towards the optical source; and
   the directional beam splitter being arranged to direct at least part of the optical radiation directed towards the optical source to the detector.

8. A measuring device as claimed in claim 7, wherein the first optical radiation processing part comprises a dispersive component that is arranged to disperse optical radiation directed to the object being measured chromatically in a non-axial direction;
   the first optical radiation processing part comprises a first focusing component that is arranged to focus the wavelengths of the non-axially dispersed optical radiation on different heights in the direction of the normal of the surface of the object being measured; and
   the second optical radiation processing part comprises a second dispersive component that is arranged to remove dispersion from the optical radiation reflected from the object being measured and to disperse the radiation reflected from the reflector chromatically in a non-axial direction;
   the second optical radiation processing part comprises a second focusing component that is arranged to focus the non-axially dispersed optical radiation reflected from the reflector on different heights in the direction of the normal of the surface being measured;
   the first optical radiation processing part is arranged to remove dispersion from the optical radiation reflected from the object being measured; and
   the directional beam splitter is arranged to direct undispersed optical radiation to the detector.

9. A measuring device as claimed in claim 7, wherein the detector is a line detector with a different wavelength of undispersed optical radiation directed to each of its elements.

10. A measuring device as claimed in claim 1, wherein the measuring device comprises a reference beam splitter and reference detector;
    the reference beam splitter is arranged to direct part of the optical radiation emitted by the optical source to the object being measured to the reference detector that is arranged to feed an electrical signal corresponding to the received optical radiation to the signal processing unit 124; and the signal processing unit is arranged to normalize the intensities of the wavelengths detected by the detector with wavelength intensities detected by the reference detector.

11. A measuring device as claimed in claim 10, wherein the directional beam splitter is arranged to act as a reference beam splitter.

12. A measuring device as claimed in claim 1, wherein the signal processing unit is arranged to modulate the optical source and demodulate the signal coming from the detector, which corresponds to the detected optical radiation.

13. A measuring device as claimed in claim 1, wherein the detector comprises a first detector part, second detector part, detector beam splitter, first filter, and second filter;
the response of the first filter is arranged to be different from that of the second filter on the measuring band;
the detector beam splitter is arranged to distribute the optical radiation reflected from the object being measured in such a manner that part of the optical radiation is directed to the first detector part through the first filter and part of it is directed to the second detector part through the second filter; and
the signal processing unit is arranged to determine from the ratio of the optical radiations detected by the first and second detector parts the wavelength with the highest intensity.

14. A measuring device for measuring the thickness of an object being measured, the measuring device comprising for the purpose of measuring a first surface:
an optical source;
an optical radiation processing unit arranged to direct different wavelengths of the optical radiation of the optical source to the object being measured from a direction differing from the normal of the surface being measured in such a manner that the different wavelengths focus on different heights in the direction of the normal of the surface being measured;
a detector to which the optical radiation processing unit is arranged to direct the optical radiation that the optical radiation processing unit is arranged to receive from the object being measured at least from the direction of specular reflection that differs from the direction of the normal of the surface being measured; and
a signal processing unit arranged to determine from the detected optical radiation on the basis of the signal provided by the detector the wavelength on which the intensity of the optical radiation is the highest and to determine the location of the surface being measured using the determined wavelength; and
the measuring device comprising for the purpose of measuring a second side of the object being measured:
a second-side optical source;
a second-side optical radiation processing unit arranged to direct different wavelengths of the optical radiation of the optical source to the object being measured from a direction differing from the normal of a second surface being measured in such a manner that the different wavelengths focus on different heights in the direction of the normal of the second surface being measured;
a second-side detector to which the optical radiation processing unit is arranged to direct the optical radiation that the radiation processing unit is arranged to receive from the object being measured at least from the direction of specular reflection that differs from the normal of the surface being measured; and
the signal processing unit is arranged to determine from the detected optical radiation on the basis of the signal provided by the second-side detector the wavelength on which the intensity of the optical radiation is the highest and to determine the location of the second surface being measured using the determined wavelength; and
the signal-processing is arranged to measure the thickness of the object being measured by means of the determined locations of the surfaces.

15. A measuring device as claimed in claim 14, wherein the measuring device comprises at least one polarizer, and at least one polarizer is arranged to polarize optical radiation reflected from the object being measured in a direction perpendicular to the normal of the surface being measured, and the measuring device comprises at least one second-side polarizer, and at least one second-side polarizer is arranged to polarize optical radiation reflected from the object being measured in a direction perpendicular to the normal of second the surface being measured.

16. A method for determining the surface of an object being measured by means of optical radiation, the method comprising
directing different wavelengths of optical radiation to the object being measured from a direction differing from the normal of the surface being measured in such a manner that the different wavelengths focus on different heights in the direction of the normal of the surface being measured;
receiving optical radiation at least from the direction of specular reflection that differs from the normal of the surface being measured;
determining from the received optical radiation the wavelength on which the intensity of the received optical radiation is the highest; and
determining the location of the surface of the object being measured by means of the determined wavelength.

17. A method as claimed in claim 16, the method further comprising polarizing the optical radiation reflected from the object being measured in a direction perpendicular to the normal of the surface being measured.

18. A method as claimed in claim 17, the method further comprising removing dispersion from the received optical radiation;
determining from the undispersed optical radiation the wavelength on which the intensity of the received optical radiation is the highest.

19. A method as claimed in claim 17, the method further comprising determining from the received dispersed optical radiation the wavelength on which the intensity of the received optical radiation is the highest.

20. A method as claimed in claim 16, the method further comprising dispersing the optical radiation directed to the object being measured chromatically in a non-axial direction;
focusing different wavelengths of the non-axially dispersed optical radiation on different heights in the direction of the normal of the surface of the object being measured while one wavelength focuses on the surface being measured.

21. A method as claimed in claim 16, the method further comprising reflecting the optical radiation reflected from the object being measured back to the object being measured in such a manner that the optical radiation is reflected from the object being measured in the direction differing from the normal of the surface being measured and used in directing; and
directing the optical radiation reflected from the object being measured for reception.

22. A method as claimed in claim 16, the method further comprising directing part of the optical radiation emitted by the optical source to the object being measured to the reference detector;
    feeding an electric signal corresponding to the optical radiation received by the reference detector to the signal processing unit 124; and
    normalizing in the signal processing unit the intensities of the wavelengths detected by the detector with the wavelength intensities detected by the reference detector.

23. A method as claimed in claim 16, the method further comprising modulating the optical radiation emitted by the optical source and correspondingly demodulating the detected signal.

24. A method for measuring the thickness of an object being measured by means of optical radiation, the method comprising
    directing different wavelengths of optical radiation to the object being measured from a direction differing from the normal of the surface being measured in such a manner that the different wavelengths are directed to different heights in the direction of the normal of the first surface being measured;
    receiving optical radiation at least from the direction of specular reflection that differs from the normal of the first surface being measured;
    determining from the received optical radiation the wavelength on which the intensity of the received optical radiation is the highest; and
    determining the location of the first surface being measured by means of the determined wavelength;
    directing different wavelengths of optical radiation to the object being measured from a direction differing from the normal of a second surface being measured in such a manner that the different wavelengths are directed to different heights in the direction of the normal of the second surface being measured;
    receiving optical radiation at least from the direction of specular reflection that differs from the normal of the second surface being measured;
    determining from the received optical radiation the wavelength on which the intensity of the received optical radiation is the highest; and
    determining the location of the second surface being measured by means of the determined wavelength; and
    determining the thickness of the object being measured using the determined locations of the surfaces.

25. A method as claimed in claim 24, the method further comprising polarizing the optical radiation reflected from the object being measured in a direction perpendicular to the normal of the second surface being measured; and
    polarizing the optical radiation reflected from the object being measured in a direction perpendicular to the normal of the first surface being measured.

* * * * *